United States Patent
Zhang

(10) Patent No.: US 8,487,132 B2
(45) Date of Patent: *Jul. 16, 2013

(54) COMPOUNDS FOR INHIBITION OF 5-HYDROXYTRYPTAMINE AND NOREPHRINE REUPTAKE OR FOR TREATMENT OF DEPRESSION DISORDERS, THEIR PREPARATION PROCESSES AND USES THEREOF

(75) Inventor: Luping Zhang, Zhuzhou (CN)

(73) Assignees: Shandong Luye Pharmaceutical Co. Ltd., Yantai (CN); Youxin Li, Zhuzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/440,608

(22) Filed: Apr. 5, 2012

(65) Prior Publication Data
US 2012/0190741 A1 Jul. 26, 2012

Related U.S. Application Data

(63) Continuation of application No. 11/917,905, filed as application No. PCT/CN2006/001370 on Jun. 16, 2006, now Pat. No. 8,178,724.

(30) Foreign Application Priority Data

Jun. 17, 2005 (CN) .......................... 2005 1 0077510
Apr. 7, 2006 (CN) .......................... 2006 1 0073308

(51) Int. Cl.
*C07C 239/00* (2006.01)
*C07C 211/00* (2006.01)
*A01N 31/00* (2006.01)
*A61K 31/045* (2006.01)
*A01N 33/02* (2006.01)
*A61K 31/13* (2006.01)

(52) U.S. Cl.
USPC ............ 564/157; 564/336; 514/730; 514/659

(58) Field of Classification Search
None
See application file for complete search history.

(56) References Cited

U.S. PATENT DOCUMENTS

| 4,535,186 | A | 8/1985 | Husbands et al. |
| 6,348,494 | B1 | 2/2002 | Yardley et al. |
| 6,673,838 | B2 | 1/2004 | Hadfield et al. |
| 8,178,724 | B2 * | 5/2012 | Zhang .......................... 564/157 |
| 2003/0158253 | A1 | 8/2003 | Yardley et al. |
| 2004/0176468 | A1 | 9/2004 | Yardley et al. |
| 2004/0181093 | A1 | 9/2004 | Kim et al. |

FOREIGN PATENT DOCUMENTS

| CN | 1706813 A | 12/2005 |
| WO | 03/042162 A1 | 5/2003 |

OTHER PUBLICATIONS

Hong-Ju et al., "Effect of gabapentin derivates on mechanical allodynia-like behaviour in a rat model of chronic sciatic constriction injury," *Bioorganic & Medicinal Chemistry Letters* 14: 2537-2541, 2004.

Yardley et al., "2-Phenyl-2-(1-hydroxycycloalkyl)ethylamine Derivatives: Synthesis and Antidepressant Activity," *J Med Chem 33*: 2899-2905, 1990.

* cited by examiner

*Primary Examiner* — Sudhakar Katakam
*Assistant Examiner* — Clinton Brooks
(74) *Attorney, Agent, or Firm* — Seed IP Law Group PLLC

(57) ABSTRACT

The present invention discloses compounds of formula (I), their optical isomers or pharmaceutically acceptable salts thereof, their preparation and uses thereof, wherein the definitions of R1, R2, R3 and R4 are shown in the description. These compounds are optical isomers or racemic mixtures. After these compounds are uptaken, they are metabolically transformated in vivo into 1-[2-dimethylamino-1-(4-hydroxyphenyl)-ethyl]-cyclohexanol that has neuropharmacological activity, by interrupting reuptake of 5-hydroxytryptamine (5-HT) and/or norepinephrine (NA), which is used for treating diseases associated with central nerve system, such as depression, etc.

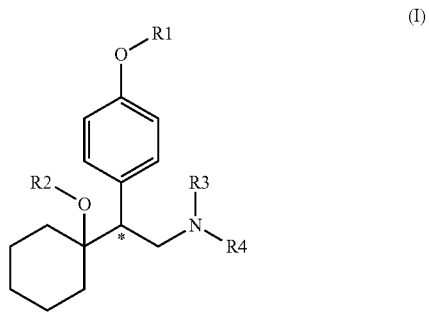

6 Claims, 2 Drawing Sheets

COMPOUNDS FOR INHIBITION OF 5-HYDROXYTRYPTAMINE AND NOREPINEPHRINE REUPTAKE OR FOR TREATMENT OF DEPRESSION DISORDERS, THEIR PREPARATION PROCESSES AND USES THEREOF

CROSS-REFERENCES TO RELATED APPLICATIONS

This application is a continuation of U.S. patent application Ser. No. 11/917,905, filed Aug. 22, 2008 (now allowed), which is a national stage application filed under 35 U.S.C. 371 of International Application No. PCT/CN2006/001370 filed Jun. 16, 2006; which claims priority to Chinese Application No. 200610073308.4 filed Apr. 7, 2006 and Chinese Application No. 200510077510.X filed Jun. 17, 2005. These applications are incorporated herein by reference in their entireties.

BACKGROUND

1. Technical Field

The present invention relates to compounds of formula (I) and salts thereof, their preparation processes, pharmaceutical compositions comprising them, and uses thereof for inhibition of 5-hydroxytryptamine (5-HT) and norepinephrine (NA) reuptake and for treatment or adjunctive therapy of central nerve system disorders, such as depression, etc.

2. Description of the Related Art

It is reported that venlafaxine of formula (II), 1-[2-dimethylamino-1-(4-methoxyphenyl)-ethyl]-cyclohexanol, is an inhibitor of 5-hydroxytryptamine (5-HT) and norepinephrine (NA) reuptake, and is widely used for treatment of depression disorders, etc. Furthermore, after the compound of formula (II) is uptaken, it is metabolized in liver to form a strongly active metabolite (III), 1-[2-dimethylamino-1-(4-hydroxyphenyl)-ethyl]-cyclohexanol and weakly active metabolites, (IV), 1-[2-methylamino-1-(4-methoxyphenyl)-ethyl]-cyclohexanol, and (V), 1-[2-methylamino-1-(4-hydroxyphenyl)-ethyl]-cyclohexanol, wherein the compounds (II) and (III) have the same therapeutic effects (see also, U.S. Pat. No. 4,535,186, US20040176468, US20040147601, US20030191347, Wyeth Effexor description).

As compared to the uptake of the compound (II), the direct uptake of the compound (III) for treating diseases related to central nerve system, especially depression, has the advantage of the principle of using a single active compound, facilitates the adjustment of dosage and therapeutic effects, alleviates side-effects, and reduces the risk of interaction with other drugs (see U.S. Pat. No. 6,673,838). However, the compound (III) with more hydroxyl groups results in the increase of hydrophilicity, and therefore decreases absorption rate via oral or transdermal and leads to possibly more pre-system side-effects due to unabsorbed drug. For overcoming the above drawbacks of the compound (III), a series of derivatives [compounds of formula (I)] of compound (III) are synthesized, and these compounds as the prodrugs of the compound (III) are metabolized in vivo to produce the compound (III), thereby exhibiting therapeutic effects.

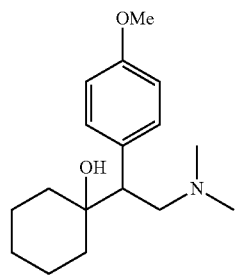

(II)

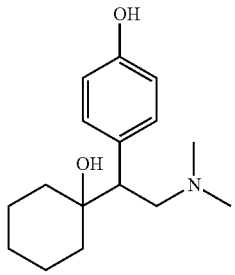

(III)

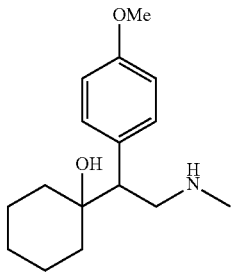

(IV)

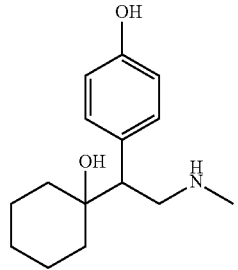

(V)

BRIEF SUMMARY

The purpose of the present invention is to develop new compounds which are used as prodrugs of inhibitor of 5-hydroxytryptamine (5-HT) and norepinephrine (NA) reuptake, and especially used for the treatment of depression, etc. The compounds of formula (I) obtained thereby have the advantage of the principle of using a single active compound, facilitate the adjustment of dosage and therapeutic effects, alleviate side-effects, reduce the risk of interaction with other drugs, elevate bioavailability, and reduce pre-system side-effects due to un-absorbed drug.

The present invention relates to compounds of formula (I), its optical isomers or pharmaceutically acceptable salts, which are used as prodrugs of inhibitors of 5-hydroxytryptamine (5-HT) and norepinephrine (NA) reuptake, and especially used for the treatment of depression, etc.

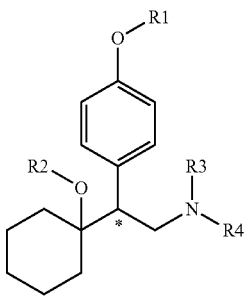

(I)

wherein,

Chiral center (*) can be R, S or RS (racemic mixture);

R1 is selected from C1-C20 saturated alkylacyl or C2-C20 unsaturated alkyloyl, preferably formyl, acetyl, propionyl, butanoyl, isobutyryl and saturated or unsaturated fatty acyl; or aryloyl having 7-20 carbon atoms, preferably benzoyl with substituent having 1 to 10 carbons or unsubstituted benzoyl; or cycloalkyloyl having 4-10 carbon atoms, or hydroxyalkyloyl or carbohydrate having 1-10 carbon atoms, as well as C1-C10 organic acyl group containing oxygen, nitrogen and fluorine, sulfur, phosphor or other heteroatoms; or the following groups:

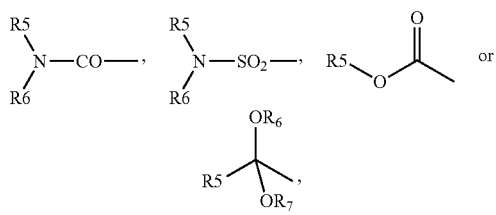

wherein R5, R6 and R7 are independently selected from hydrogen, saturated alkyl having 1-10 carbon atoms or unsaturated alkyl having 2-20 carbon atoms, or aryl having 7-20 carbon atoms, such as phenyl or benzyl with substituent having 1 to 10 carbons or unsubstituted phenyl or benzyl, etc.;

R2 is selected from hydrogen, saturated alkyl having 1-20 carbon atoms, unsaturated alkyl having 2-20 carbon atoms, aryl having 6-20 carbon atoms, cycloalkyl having 4-10 carbon atoms, hydroxyalkyl or carbohydrate substituent having 1-10 carbon atoms, saturated alkyloyl having 1-20 carbon atoms, unsaturated alkyloyl having 2-20 carbon atoms, preferably formyl, acetyl, propionyl, butanoyl, isobutyryl and unsaturated fatty acyl; aryloyl having 7-20 carbon atoms, preferably benzoyl with substituent having 1 to 10 carbons or unsubstituted benzoyl; cycloalkyloyl having 4-10 carbon atoms, hydroxyalkyloyl having 1-10 carbon atoms, C1-C10 organic acyl group containing oxygen, nitrogen and fluorine, sulfur, phosphor or other heteroatoms; or the following groups:

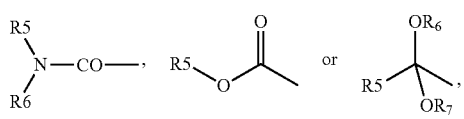

wherein R5, R6 and R7 are independently selected from hydrogen, saturated alkyl having 1-20 carbon atoms, unsaturated alkyl having 2-20 carbon atoms, or aryl having 6-20 carbon atoms, such as phenyl or benzyl with substituent having 1 to 10 carbons or unsubstituted phenyl or benzyl, etc.;

R3 and R4 are independently selected from hydrogen, saturated alkyl having 1-20 carbon atoms, unsaturated alkyl having 2-20 carbon atoms, aryl having 6-20 carbon atoms such as phenyl or benzyl with substituent having 1 to 10 carbons or unsubstituted phenyl or benzyl; cycloalkyl having 4-10 carbon atoms, hydroxyalkyl or carbohydrate having 1-10 carbon atoms, as well as C1-C10 organic alkyl containing oxygen, nitrogen and fluorine, sulfur, phosphor or other heteroatoms, etc.;

preferably, R1 is aryloyl having 7-20 carbon atoms, alkoxyloyl having 1-10 carbon atoms or aryloxyloyl having 7-10 carbon atoms, 1,1-dialkoxylalkyl having 1-10 carbon atoms, and alkylaminocarbonyl having 1-10 carbon atoms; R2 is hydrogen; R3 and R4 are methyl.

The above arylacyl preferably is

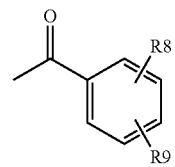

wherein, R8 and R9 are independently selected from hydrogen, saturated alkyl having 1-6 carbon atoms, or alkoxyl having 1-6 carbon atoms, unsaturated alkyl having 2-6 carbon atoms, OH, Cl, F, CN, carboxyl and ester group; preferably hydrogen, methyl, ethyl, methoxy, ethoxy, fluorine or carboxyl.

According to the present invention, the term "optical isomers" refers to the R or S optical isomers or RS racemic mixtures of the compounds (I) or their pharmaceutically acceptable salts.

According to the present invention, representative compounds of formula (I) are:

4-[2-Dimethylamino-1-(1-hydroxycyclohexyl)-ethyl]-phenyl benzoate

4-[2-Dimethylamino-1-(1-hydroxycyclohexyl)-ethyl]-phenyl 4-methylbenzoate

4-[2-Dimethylamino-1-(1-hydroxycyclohexyl)-ethyl]-phenyl 4-methoxybenzoate

4-[2-Dimethylamino-1-(1-hydroxycyclohexyl)-ethyl]-phenyl 4-fluorobenzoate

4-[2-Dimethylamino-1-(1-hydroxycyclohexyl)-ethyl]-phenyl 2-carboxylbenzoate

4-[2-Dimethylamino-1-(1-benzoyloxycyclohexyl)-ethyl]-phenyl benzoate

4-[2-Dimethylamino-1-(1-(4-methyl)benzoyloxycyclohexyl)-ethyl]-phenyl 4-methylbenzoate 4-[2-Dimethylamino-1-(1-(4-methoxy)benzoyloxycyclohexyl)-ethyl]-phenyl 4-methoxybenzoate 4-[2-Dimethylamino-1-(1-(4-fluoro)benzoyloxycyclohexyl)-ethyl]-phenyl 4-fluorobenzoate 4-[2-Dimethylamino-1-(1-benzoyloxycyclohexyl)-ethyl]-phenyl 4-methylbenzoate 1-[2-Dimethylamino-1-(1-benzoyloxycyclohexyl)-ethyl]-cyclohexyl 4-methoxybenzoate 4-[2-Dimethylamino-1-(1-(4-methoxy)benzoyloxycyclohexyl)-ethyl]-phenyl 4-methylbenzoate 4-[2-Dimethylamino-1-(1-benzoyloxycyclohexyl)-ethyl]-phenyl N-methylcarbamate 4-[2-Dimethylamino-1-(1-benzoyloxycyclohexyl)-ethyl]-phenyl N,N-dimethylcarbamate 4-[2-Dimethylamino-1-(1-benzoyloxycyclohexyl)-ethyl]-phenyl ethylcarbonate and their various salts and optical isomers.

According to conventional methods for manufacture of medicaments in the art, the compounds of formula (I) of the present invention including their optical isomers and racemic mixtures as well as pharmaceutically acceptable salts thereof can be processed to form appropriate dosage forms, such as dosage forms for oral, injection, transdermal, nasal, mucous and inhalation administration. The dosage forms for oral administration can be solid tablets or capsules or soft capsules or drop pills, as well as solutions or suspensions or emulsions or powders, can be normal dosage forms or sustained release or site specific delivery or fast release or disintegrating dosage forms. The dosage forms for injection administration can be intravenous injection or subcutaneous injection or intramuscular injection or intraperitoneal injection, can be solutions or suspensions or emulsions, and can be normal or long acting dosage forms such as implants, microspheres or gels. The dosage forms for transdermal administration can be transdermal patch, gels or other forms. Inhalation administration can be solutions, suspensions, emulsions or powders. The dosage forms for mucous administration can be solutions suspensions, emulsions, powders or suppositories.

The present invention further relates to pharmaceutical compositions comprising an effective amount of compound of formula (I), and compatible and pharmaceutically acceptable carriers or diluents. The carriers can be any inert organics or inorganics, such as water, gelatin, cellulose, starch, etc., or other pharmaceutically active substances, and other conventional additives, such as stabilizers, moistening agents, emulsifiers, flavoring agents and buffers, etc.

The compounds of formula (I) of the present invention including their optical isomers and racemic mixtures as well as pharmaceutically acceptable salts thereof can be used for treatment of relevant diseases or disorders, for example, depression, anxiety disorders, generalized anxiety disorders, panic-stricken, agoraphobia, post-traumatic stress disorders, premenstrual dysphoric disorders, fibromyalgia, impaired concentration, obsessive-compulsive syndrome, social anxiety disorders, autistic disorders, schizophrenia, obesity, hyperorexia nervosa and anorexia nervosa, Tourette syndrome, vasomotor flush, cocaine or alcohol addiction, sexual disturbance, borderline personality disorder, chronic fatigue syndrome, urinary incontinence, pains, Shy Drager syndrome, Raynaud syndrome, Parkinson's disease, and epilepsy, etc., by single or multiple dosage of 1 mg to 1000 mg per day.

DETAILED DESCRIPTION

Figure 1A:
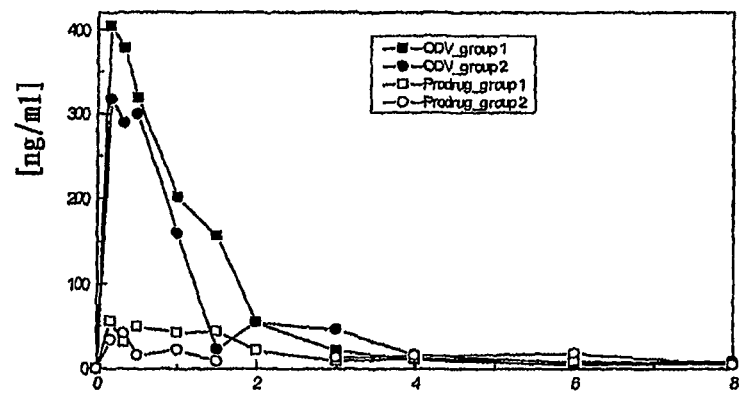
FIG. 1 shows the metabolism in vivo of the prodrug 4-[2-dimethylamino-1-(1-hydroxycyclohexyl)-ethyl]-phenyl 4-methylbenzoate hydrochloride in rats, wherein A represents intravenous administration, B represents oral administration; in Group I, □ represents the prodrug: 4-[2-dimethylamino-1-(1-hydroxycyclohexyl)-ethyl]-phenyl 4-methylbenzoate, and ■ represents active metabolite: the compound (III); in Group II, ○ represents the prodrug: 4-[2-dimethylamino-1-(1-hydroxycyclohexyl)-ethyl]-phenyl 4-methylbenzoate, and ● represents active metabolite: the compound (III).

The present invention is further illustrated, but not restricted by the following examples.

2.52 g (10 mmol) the compound (III) and 9.98 mmol organic acyl chloride were added into 100 mL dichloromethane, stirred and cooled to 0° C. 1.05 g (9.9 mmol) of triethylamine in dichloromethane solution was added dropwise (about ten minutes), then continuously stirred at room temperature for 18 hours. The reaction solution was washed with 50 mL water and separated, then the organic phase was dried with anhydrous sodium sulfate, the solvent was removed by vacuum evaporation, and the product was dried under vacuum.

Formation of Salt (e.g., Hydrochloride) of the Compound VI 30 mL anhydrous aether solution containing 5 mmol the above product was cooled to 0° C., and then 1M aether solution containing 4.8 mmol hydrogen chloride was added under nitrogen gas. The oily precipitation was washed with anhydrous aether repetitively, and then dried under vacuum. Most products were amorphous foam-like solids.

According to the above reaction scheme, the following compounds were synthesized and characterized.

EXAMPLE 1

Synthesis of Carboxylic Acid Phenyl Monoester [Formula (VI)] of the Compound (III)

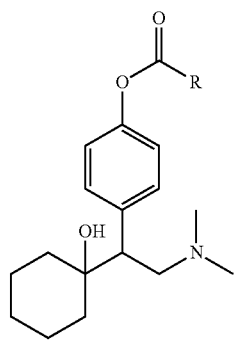

(VI)

The compound (III) was synthesized according to U.S. Pat. No. 4,535,186.

General Methods and Processes
General reaction formula:

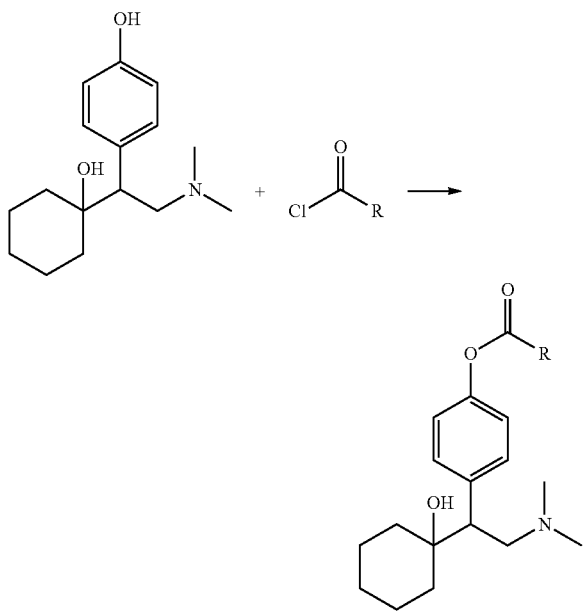

wherein R is phenyl, tolyl, methoxyphenyl, or other aryl, etc.

4-[2-dimethylamino-1-(1-hydroxycyclohexyl)-ethyl]phenyl 4-methylbenzoate was taken as an example.

10 g desmethyl-venlafaxine (compound III) was dissolved in 200 ml anhydrous pyridine, and cooled to 0° C. Equimolar 4-Methylbenzoyl chloride dissolved in anhydrous tetrahydrofuran was added dropwise, and reaction was conducted at this temperature under stirring for 5 hours. Then, the most of solvent was removed by vacuum evaporation. The residue was poured into 400 ml water, adjusted under stirring until pH was 9, and stored overnight. The precipitated solid was filtered out, washed with water for three times, and dried to obtain a crude product. The crude product was recrystallized with 80 ml anhydrous ethanol/ethyl acetate (1:1) to obtain 8.0 g white solid with a melting point of 159.0-162.2° C. and a yield of 55.2%.

Preparation of hydrochloride: 20 ml anhydrous ethanol was added to 2.0 g of the above product, concentrated hydrochloric acid was added dropwise until all the product was dissolved, then solvent was removed by vacuum evaporation, the product was washed with anhydrous ethanol for three times and dissolved by adding ethyl acetate. The precipitated solid was filtered out to obtain 2.0 g white crystal solid having a melting point of 203.2-206.5° C.

According to this method, the following compounds were synthesized and characterized.

Compound 1: 4-[2-dimethylamino-1-(1-hydroxycyclohexyl)-ethyl]phenyl 4-methylbenzoate $^1$H-NMR (DMSO) δ1.14-1.59 (10H, m, —(CH$_2$)$_5$—), 2.11 (6H, s, —N(CH$_3$)$_2$), 2.42 (3H, s, Ar—CH$_3$), 2.55 (1H, m, —CH<), 2.86 (2H, m, —CH$_2$—N—), 5.02 (1H, br, —OH), 7.11, 7.27, 7.40, 8.00 (8H, d, d, d, d, Ar—H);
$^{13}$C-NMR (DMSO) 21.40, 21.65 (2C), 24.79, 39.89, 40.81 (2C), 45.89 (2C), 57.94, 76.57, 120.19 (2C), 123.01 (2C), 126.42, 127.95 (2C), 128.13 (2C), 136.97, 141.90, 147.42, 164.18;
Melting point: 159.0-162.2° C., Melting point of its hydrochloride: 203.2-206.5° C.

Compound 2: 4-[2-dimethylamino-1-(1-hydroxycyclohexyl)-ethyl]phenyl benzoate

All reaction conditions were the same, except that 4-methylbenzoyl chloride was replaced with benzoyl chloride.
$^1$H-NMR (DMSO) δ 0.97-1.61 (10H, m, —(CH$_2$)$_5$—), 2.12 (6H, s, —N(CH$_3$)$_2$), 2.57 (1H, t, >CH—), 2.84 (2H, m, —CH$_2$—N—), 4.98 (1H, br, —OH), 7.13-8.13 (9H, m, Ar—H);
$^{13}$C-NMR (DMSO) 21.65 (2C), 24.79, 39.89, 40.81 (2C), 45.89 (2C), 57.94, 76.57, 120.19 (2C), 123.01 (2C), 125.92, 128.80 (2C), 132.99 (2C), 133.85, 136.97, 147.42, 164.18;
Melting point: 176.3-179.1° C., melting point of its hydrochloride: 206.6-207.7° C.

Compound 3: 4-[2-dimethylamino-1-(1-hydroxycyclohexyl)-ethyl]phenyl 4-methoxybenzoate All reaction conditions were the same, except that 4-methylbenzoyl chloride was replaced with 4-methoxybenzoyl chloride.
$^1$H-NMR (DMSO) M 0.14-1.59 (10H, m, —(CH$_2$)$_5$—), 2.11 (6H, s, —N(CH$_3$)$_2$), 2.55 (1H, m, —CH<), 2.86 (2H, m, —CH$_2$—N—), 3.86 (3H, s, —OCH$_3$), 5.02 (1H, br, —OH), 7.10, 7.26, 8.06 (8H, t, d, d, Ar—H);
$^{13}$C-NMR (DMSO) 21.65 (2C), 24.79, 39.89, 40.81 (2C), 45.89 (2C), 55.25, 57.94, 76.57, 113.14 (2C), 120.19 (2C), 122.52, 123.01 (2C), 132.28 (2C), 137.01, 147.42, 162.50, 164.18;
Melting point: 133.4-135.7° C., melting point of its hydrochloride: 195.7-196.9° C.

Compound 4: 4-[2-dimethylamino-1-(1-hydroxycyclohexyl)-ethyl]phenyl 4-fluorobenzoate All reaction conditions were the same, except that 4-methylbenzoyl chloride was replaced with 4-fluorobenzoyl chloride.
$^1$H-NMR (DMSO) δ1.25-1.59 (10H, m, —(CH$_2$)$_5$—), 2.16 (6H, s, —N(CH$_3$)$_2$), 2.55 (1H, m, —CH<), 2.86 (2H, m, —CH$_2$—N—), 5.02 (1H, br, —OH), 7.00, 7.16, 7.26, 8.12 (8H, t, d, d, Ar—H);
$^{13}$C-NMR (DMSO) 21.65 (2C), 24.79, 39.90, 40.81 (2C), 45.90 (2C), 57.94, 76.57, 114.41, 115.12, 120.19 (2C), 123.02 (2C), 130.91, 131.08, 137.02, 147.42, 158.38, 164.19, 164.88;
Melting point: 146.2-148.5° C., melting point of its hydrochloride: 199.2-201.3° C.

EXAMPLE 2

Synthesis of Carboxylic Acid Diester [Formula (VII)] of the Compound (III)

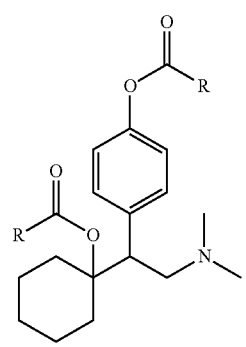

(VII)

General reaction formula:

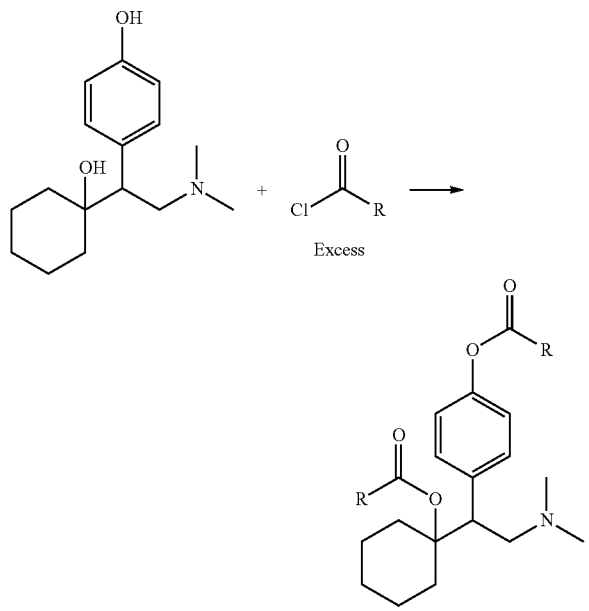

wherein R is phenyl, tolyl, methoxyphenyl, or other aryl or alkyl, etc.

The synthesis method was identical to that of the Example 1, except that twice or more amount of organic acyl chloride and triethyl amine were added.

4-[2-dimethylamine-1-(1-benzoyloxycyclohexyl)-ethyl]-phenyl benzoate was taken as an example.

17.4 g desmethyl-venlafaxine (compound III), 18.58 g benzoyl chloride and 200 ml anhydrous tetrahydrofuran were added into a reaction flask, and cooled to 0° C. 50 mL anhydrous tetrahydrofuran solution of triethylamine was added dropwise. After all raw materials were dissolved, the reaction solution was poured into 400 mL water and stirred. Then the precipitated solid was filtered out, washed with water for three times, and dried to obtain a crude product. The crude product was then dissolved in 10 times amount of anhydrous ethanol and recrystallized to obtain 19.3 g white solid having a melting point of 127.8-129.7° C. and a yield of 60.9%.

Preparation of hydrochloride: 5.0 g of the above product was dissolved in 20 ml anhydrous ether, then anhydrous saturated ether solution of hydrogen chloride was added dropwise. The precipitated solid was filtered out to obtain 5.0 g white crystal solid having melting point of 176.1-179.0° C.

According to this method, the following compounds were synthesized.

Compound 2.1: 4-[2-dimethylamino-1-(1-benzoyloxycyclohexyl)-ethyl]phenyl benzoate $^1$H NMR (DMSO) δ 1.07-1.58 (10H, m, —$(CH_2)_5$—), 2.01 (6H, s, —$N(CH_3)_2$), 2.33, 4.06 (2H, dd, —$CH_2$—N—), 3.00 (1H, t, —CH<), 7.16-8.13 (14H, m, Ar—H), $^{13}$C-NMR (DMSO) 21.56 (2C), 24.64, 37.70 (2C), 37.94, 45.89 (2C), 57.85, 81.50, 120.35 (2C), 123.37 (2C), 125.90, 128.67 (2C), 128.80 (2C), 129.42, 129.47 (2C), 132.86, 132.99 (2C), 133.85, 136.41, 148.19, 164.18, 166.21;

Melting point: 127.8-129.7° C., melting point of its hydrochloride: 176.1-179.0° C.

Compound 2.2: 4-[2-dimethylamino-1-(1-(4-methyl)benzoyloxycyclohexyl)-ethyl]phenyl 4-methylbenzoate The reaction conditions were the same, except that benzoyl chloride was replaced with 4-methylbenzoyl chloride.

$^1$H-NMR (DMSO) δ1.10-1.59 (10H, m, —$(CH_2)_5$—), 2.11 (6H, s, —$N(CH_3)_2$), 2.45 (6H, s, Ar—$CH_3$), 2.55 (1H, m, —CH<), 2.86 (2H, m, —$CH_2$—N—), 7.11-8.00 (12H, d, d, d, d, Ar—H);

$^{13}$C-NMR (DMSO) 21.40 (2C), 21.56 (2C), 24.64, 37.70 (2C), 37.94, 45.89 (2C), 57.85, 81.50, 120.35 (2C), 123.42 (2C), 125.31, 126.43, 127.59 (2C), 127.95 (2C), 128.10 (2C), 128.13 (2C), 136.41, 141.90 (2C), 148.19, 164.19, 166.21;

Melting point: 122.8-125.1° C.

Compound 2.3: 4-[2-dimethylamino-1-(1-(4-methoxy)benzoyloxycyclohexyl)-ethyl]phenyl 4-methoxybenzoate The reaction conditions were the same, except that benzoyl chloride was replaced with 4-methoxybenzoyl chloride.

$^1$H-NMR (DMSO) δ1.14-1.59 (10H, m, —$(CH_2)_5$—), 2.11 (6H, s, —$N(CH_3)_2$), 2.55 (1H, m, —CH<), 2.86 (2H, m, —$CH_2$—N—), 3.86 (6H, s, —$OCH_3$), 5.02 (1H, br, —OH), 7.10-8.06 (12H, t, d, d, Ar—H);

$^{13}$C-NMR (DMSO) 21.56 (2C). 24.64, 37.70 (2C), 37.94, 45.89 (2C), 55.25 (2C), 57.85, 81.50, 113.11 (2C), 113.14 (2C), 120.35 (2C), 121.03, 122.52, 123.37 (2C), 131.21 (2C), 132, 28 (2C), 136.41, 148.19, 162.50 (2C), 164.16, 166.21;

Melting point: 112.6-114.9° C.

EXAMPLE 3

Synthesis of Carboxylic Acid Asymmetric Diester [Formula (VIII)] of the Compound (III)

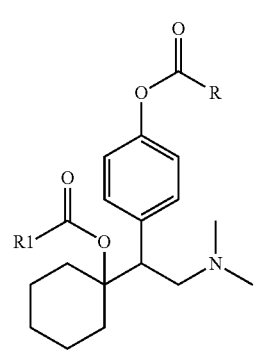

(VIII)

R ≠ R1

The asymmetric diester was obtained by acylating corresponding monoester, and the synthesis thereof was identical to that of Example 1.

The general formula of reaction:

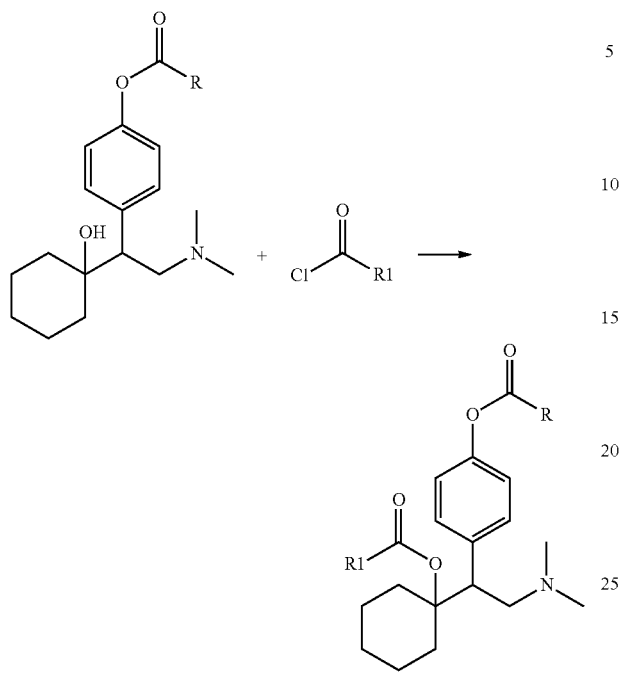

wherein R, R1 are phenyl, tolyl, methoxyphenyl, or other aryl or alkyl, etc.

4-[2-dimethylamino-1-(1-benzoyloxycyclohexyl)-ethyl]phenyl 4-methylbenzoate was taken as an example.

10 mmol of the monoester (Compound 1 of Example 1) synthesized according to Example 1 and 10-15 mmol benzoyl chloride were added into 200 mL anhydrous pyridine, and cooled to 0° C. under stirring, then anhydrous tetrahydrofuran solution containing 1.05 g (9.9 mmol) triethylamine was added dropwise (about 10 minutes), and the reaction was continuously conducted at room temperature under stirring for 18 hours. The reaction solution was washed with 50 ml water and separated, then the organic phase was dried with anhydrous sodium sulfate, and then the solvent was removed by vacuum evaporation, the residue was poured into 400 mL water, adjusted under stirring until pH was 9, and stored overnight. The precipitated solid was filtered out, washed with water for three times, and dried to obtain a crude product. The crude product was recrystallized with anhydrous ethanol to obtain a white solid.

The following compounds were synthesized according to this method.

Compound 3.1: 4-[2-dimethylamino-1-(1-benzoyloxycyclohexyl)-ethyl]phenyl 4-methylbenzoate $^1$H-NMR (DMSO) δ1.10-1.59 (10H, m, —(CH$_2$)$_5$—), 2.17 (6H, s, —N(CH$_3$)$_2$), 2.42 (3H, s, Ar—CH$_3$), 2.55 (1H, m, —CH<), 2.86 (2H, m, —CH$_2$—N—), 7.11-8.20 (13H, d, d, d, d, Ar—H);

$^{13}$C-NMR (DMSO) 21.40, 21.56 (2C), 24.64, 37.70 (2C), 37.94, 45.89 (2C), 57.86, 81.52, 120.36 (2C), 123.38 (2C), 126.43, 127.95 (2C), 128.13 (2C), 128.67 (2C), 129.42, 129.47 (2C), 132.86, 136.41, 141.90, 149.19, 164.19, 166.22;

Melting point: 127.8-130.2° C.

Compound 3.2: 4-[2-dimethylamino-1-(1-benzoyloxycyclohexyl)-ethyl]phenyl 4-methoxybenzoate The reaction conditions were the same, except that the compound 1 of Example 1 was replaced with the compound 3 of Example 1.

$^1$H-NMR (DMSO) δ1.22-1.76 (10H, m, —(CH$_2$)$_5$—), 2.15 (6H, s, —N(CH$_3$)$_2$), 2.58 (1H, m, —CH<), 2.76 (2H, m, —CH$_2$—N—), 3.86 (3H, s, —OCH$_3$), 7.16-8.10 (9H, t, d, d, Ar—H);

$^{13}$C-NMR (DMSO) 21.56 (2C), 24.64, 37.70 (2C), 37.94, 45.89 (2C), 55.25, 57.85, 81.50, 113.12 (2C), 120.35 (2C), 121.03, 123.37 (2C), 125.92, 128.81 (2C), 131.22 (2C), 132.99 (2C), 133.85, 136.41, 148.19, 162.50, 164.18, 166.26;

Melting point: 119.6-122.8° C.

EXAMPLE 4

Syntheses of Carbamoylphenyl Monoester [Formula (IX)] of the Benzyl Ether of the Compound (III)

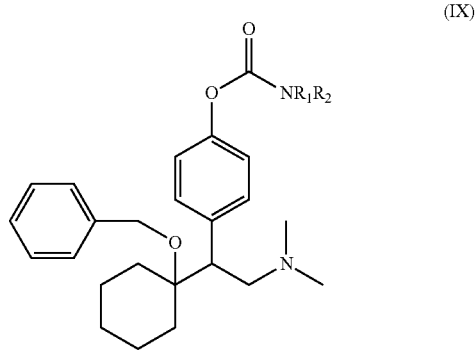

The general formula of reaction:

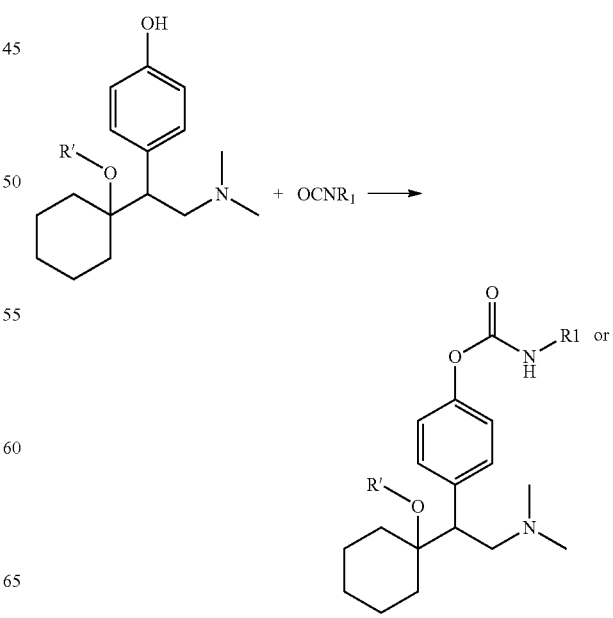

-continued

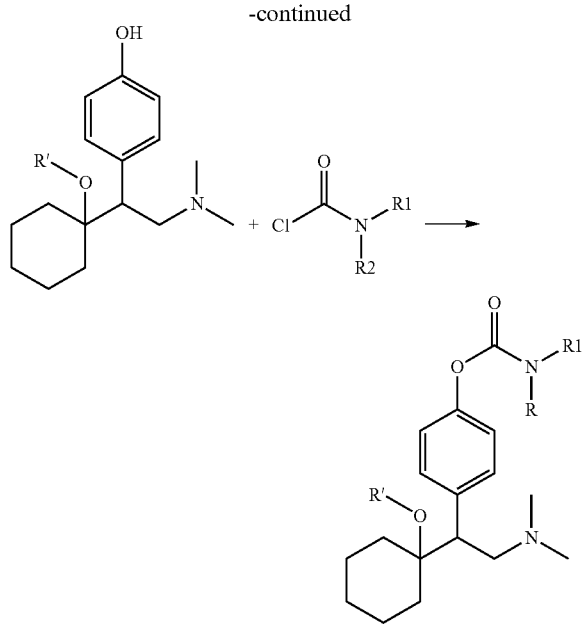

wherein R1, R2 or R' are H, methyl, ethyl, propyl, isopropyl, phenyl, tolyl or other alkyl or aryl, etc.

Compound 4.1: 4-[2-dimethylamino-1-(1-benzyloxycyclohexyl)-ethyl]phenyl N-methyl-carbamate 6 mmol methyl isocyanate was added under stirring into 20 mL dichloromethane solution containing 5 mmol benzyl ether of the compound (III), the reaction was conducted at room temperature for 16 hours, then the reaction solution was washed with 10 mL 5% sodium bicarbonate aqueous solution, dried with anhydrous sodium sulfate, and the solvent was removed by evaporation to obtain an oily or white solid product.

$^1$H-NMR (DMSO) 1.33-1.69 (10H, m, —(CH$_2$)$_5$—), 2.17 (6H, s, —N(CH$_3$)$_2$), 2.65 (1H, m, —CH<), 2.76 (2H, m, —CH$_2$—N—), 2.78 (3H—NCH$_3$), 5.37 (NH), 6.90-7.59 (9H, Ar—H);
$^{13}$C-NMR (DMSO) 22.43 (2C), 25.22, 27.35, 35.14, 39.29 (2C), 45.89 (2C), 56.72, 81.67, 120.30 (2C), 122.81 (2C), 122.89, 124.36 (2C), 128.81 (2C), 135.34, 147.41, 156.11, 160.37; melting point: 138.6-140.8° C.

Compound 2: 4-[2-dimethylamino-1-(1-benzyloxycyclohexyl)-ethyl]phenyl N,N-dimethyl-carbamate 6 mmol N-dimethyl-formyl chloride was added at 0° C. under stirring into 30 mL dichloromethane solution containing 5 mmol benzyl ether derivate of the compound (III) and 1 mL triethylamine, the reaction was continuously conducted at 0° C. for 6 hours, then the reaction liquid was washed with 10 mL 5% sodium bicarbonate aqueous solution, dried with anhydrous sodium sulfate, and the solvent was removed by evaporation to obtain an oily or white sodium product.

$^1$H-NMR (DMSO) 1.33-1.69 (10H, m, —(CH$_2$)$_5$—), 2.17 (6H, s, —N(CH$_3$)$_2$), 2.65 (1H, m, —CH<), 2.76 (2H, m, —CH$_2$—N—), 2.89 (6HN(CH$_3$)$_2$), 6.90-7.59 (9H, Ar—H).
$^{13}$C-NMR (DMSO) 20.43 (2C), 25.15, 35.14, 36.42, 36.65, 39.29 (2C), 45.89 (2C), 56.72, 81.67, 1220.70 (2C), 122, 80 (2C), 122.90, 124.71 (2C), 128.81 (2C), 135.45, 148.50, 155.12, 156.11;

Melting point: 126.2-129.3° C.

EXAMPLE 5

Experiment of Compound Metabolism in Liver Cells to Form the Active Component 1-[2-Dimethylamino-1-(4-Hydroxyphenyl)-Ethyl]-Cyclohexanol (the Compound III)

40 μg the compound 1 (or the compound 2 or 3 or 4) of Example 1 was dissolved into 0.01M potassium phosphate buffer solution containing 1 mM NADPH, mixed with 25 μL human liver cells S9 (20 mg protein/mL, H961), and cultured at 37° C. for 2 hours. Then the mixture was quenched with concentrated perchloric acid. After the precipitated proteins were removed by centrifuge, the supernatant was adjusted with concentrated potassium phosphate until pH was 3, and centrifuged again. The supernatant was directly injected into HPLC and analyzed.

The results of metabolism are shown in Table 1. The metabolic rates from the compounds to the active component 1-[2-dimethylamino-1-(4-hydroxyphenyl)-ethyl]cyclohexanol (compound III) in liver cells within 2 hours range from 80% to 100%, respectively, depending on different ester groups.

TABLE 1

Metabolic rate of compounds in liver cells within 2 hours

| X/Y | Compound 1 of Example 1 | Compound 2 of Example 1 | Compound 3 of Example 1 | Compound 4 of Example 1 |
|---|---|---|---|---|
| Metabolic rate (%) | 99 | 96 | 92 | 88 |

EXAMPLE 6

Metabolic Experiments of 4-[2-Dimethylamino-1-(1-Hydroxycyclohexyl)-Ethyl]Phenyl 4-Methylbenzoate (the Compound 1 of Example 1) Vial Oral and Intravenous Administration in Rats Six rats were divided into two groups, and were subjected to intragastric or intravenous administration of 4-[2-dimethylamino-1-(1-hydroxycyclohexyl)-ethyl]phenyl 4-methylbenzoate hydrochloride in a dose of 13.5 mg/kg. Blood samples were sampled according to the predetermined schedules, and the concentrations of the prodrug 4-[2-dimethylamino-1-(1-hydroxycyclohexyl)-ethyl]phenyl 4-methylbenzoate and the active metabolite 1-[2-dimethylamino-1-(4-hydroxyphenyl)-ethyl]cyclohexanol (compound III) in blood were measured.

The results of intravenous administration in rats (see FIG. 1A) indicate that the prodrug 4-[2-dimethylamino-1-(1-hydroxycyclohexyl)-ethyl]phenyl 4-methylbenzoate hydrochloride was quickly metabolized in blood of rats, and the active metabolite 1-[2-dimethylamino-1-(4-hydroxyphenyl)-ethyl]cyclohexanol (compound III) (ODV) reached Cmaxat 30 minutes, and in the meantime, the concentration of the prodrug in blood was only 10-15% of its active metabolite 1-[2-dimethylamino-1-(4-hydroxyphenyl)-ethyl]cyclohexanol (compound III) (ODV) and decreased continuously.

Figure 1B:
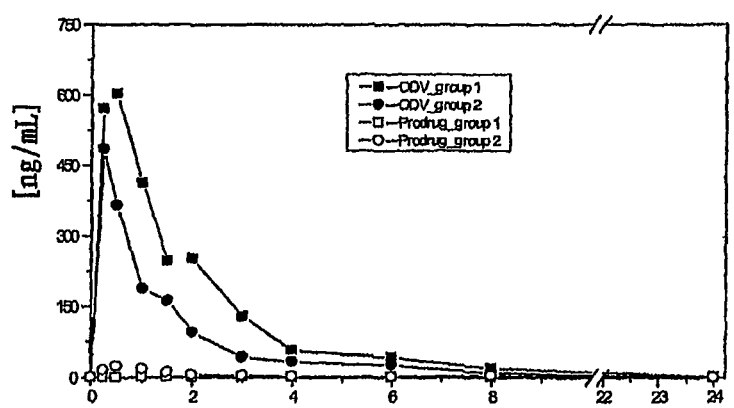

The results of oral administration are shown in FIG. 1B. After the prodrug entered into body through gastrointestinal tract, it was metabolized immediately to form the active metabolite 1-[2-dimethylamino-1-(4-hydroxyphenyl)-ethyl] cyclohexanol (compound III) (ODV) with higher rate and degree and lower prodrug concentration. The prodrug via oral administration was substantively totally converted into the desired active metabolite 1-[2-dimethylamino-1-(4-hydroxyphenyl)-ethyl]cyclohexanol (compound III), which sufficiently confirmed the metabolizability of the prodrug 4-[2-dimethylamino-1-(1-hydroxycyclohexyl)-ethyl]phenyl 4-methylbenzoate. By calculation, the bioavailability of the prodrug 4-[2-dimethylamino-1-(1-hydroxycyclohexyl)-ethyl]phenyl 4-methylbenzoate hydrochloride via oral administration in rats was above 80%, which was obviously higher than the bioavailabilies of 1-[2-dimethylamino-1-(4-hydroxyphenyl)-ethyl]-cyclohexanol (compound III) (ODV) and its various salts directly administrated orally.

EXAMPLE 7

Experimental Results of 1-[2-Dimethylamino-1-(4-Hydroxyphenyl)-Ethyl]Cyclohexanol (Compound III) Succinate and its Prodrugs 4-[2-Dimethylamino-1-(1-Hydroxycyclohexyl)-Ethyl]-Phenyl Benzoate Hydrochloride (the compound 2 of example 1)

4-[2-Dimethylamino-1-(1-Hydroxycyclohexyl)-Ethyl]Phenyl 4-Methylbenzoate Hydrochloride (the Compound 1 of Example 1), and 4-[2-Dimethylamino-1-(1-Hydroxycyclohexyl)-Ethyl]Phenyl 4-Methoxybenzoate (the Compound 3 of Example 1) Succinate in Beagles Via Oral Administration Nine beagles with body weight of about 10 kg were divided into three groups, and were subjected to intragastric administration of O-desmethyl-venlafaxine (ODV) succinate, 4-[2-dimethylamino-1-(1-hydroxycyclohexyl)-ethyl]phenyl benzoate hydrochloride, 4-[2-dimethylamino-1-(1-hydroxycyclohexyl)-ethyl]phenyl 4-methylbenzoate hydrochloride, and 4-[2-dimethylamino-1-(1-hydroxycyclohexyl)-ethyl]phenyl 4-methoxybenzoate succinate in dose of 0.016 mmol/kg. Blood samples were sampled according to the predetermined schedules, and the concentrations of the active metabolite 1-[2-dimethylamino-1-(4-hydroxyphenyl)-ethyl]cyclohexanol (compound III) and its prodrugs in blood were measured.

Figure 2:
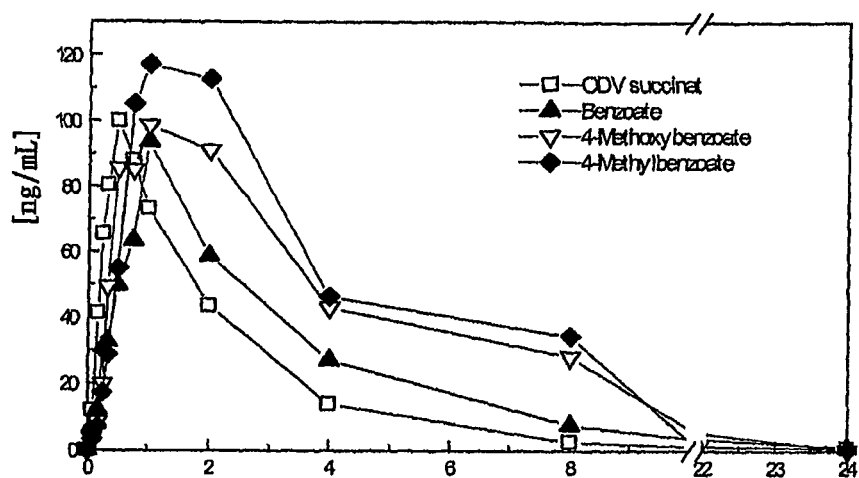
FIG. 2 shows the in vivo absorption and metabolism of 1-[2-dimethylamino-1-(4-hydroxyphenyl)-ethyl]-cyclohexanol (the compound III) succinate (ODV succinate) (represented by -□-) and its prodrugs: 4-[2-dimethylamino-1-(1-hydroxycyclohexyl)-ethyl]-phenyl benzoate hydrochloride (Benzoate) (represented by -▲-), 4-[2-dimethylamino-1-(1-hydroxycyclohexyl)-ethyl]-phenyl 4-methylbenzoate hydrochloride (4-Methylbenzoate) (represented by -◆-), and 4-[2-dimethylamino-1-(1-hydroxycyclohexyl)-ethyl]-phenyl 4-methoxybenzoate succinate (4-Methoxybenzoate) (represented by -∇-), in Beagles, wherein all blood concentrations are of active metabolite compound (III).

The results are shown in FIG. 2. After the prodrugs entered into bodies of beagles through gastrointestinal tract, they were immediated metabolized into the active metabolite desmethyl-venlafaxine, and the prodrug concentrations were lower than the measurement limit, so that it was deemed that almost all prodrugs by oral administration were converted into the desired active metabolite 1-[2-dimethylamino-1-(4-hydroxyphenyl)-ethyl]cyclohexanol (compound III). In the meantime, the results indicate that the bioavailabilities of prodrugs of ODV were obviously higher than that of ODV succinate which has the best bioavailability among ODV salts, and AUC was elevated more than 30% (Table 2), wherein the AUC of 4-[2-dimethylamino-1-(1-hydroxycyclohexyl)-ethyl]phenyl 4-methylbenzoate hydrochloride was elevated more than 60% (Table 2), the bioavailability was improved very significantly, and it exhibited obvious advantages over 1-[2-dimethylamino-1-(4-hydroxyphenyl)-ethyl] cyclohexanol (compound III) succinate.

TABLE 2

Comparison of experiment results in beagles between prodrugs and 1-[2-dimethylamino-1-(4-hydroxyphenyl)-ethyl]cyclohexanol (compound III) succinate - the concentration of the active metabolite 1-[2-dimethylamino-1-(4-hydroxyphenyl)-ethyl]cyclohexanol (compound III)

| Compound | Cmax ng/ml | Tmax hr | AUC ng/ml hr | AUC Increment rate % (ODV succinate, =100%) |
|---|---|---|---|---|
| ODV succinate | 100 | 0.5 | 261 | 100 |
| 4-[2-dimethylamino-1-(1-hydroxycyclohexyl)-ethyl]phenyl benzoate hydrochloride | 93 | 1.0 | 342 | 132 |
| 4-[2-dimethylamino-1-(1-hydroxycyclohexyl)-ethyl]phenyl 4-methylbenzoate hydrochloride | 117 | 1.0 | 421 | 161 |
| 4-[2-dimethylamino-1-(1-hydroxycyclohexyl)-ethyl]phenyl 4-methoxybenzoate succinate | 97 | 1.0 | 386 | 148 |

EXAMPLE 8

Preparation of Normal Oral Tablets

Composition:

| | |
|---|---|
| 4-[2-dimethylamino-1-(1-hydroxycyclohexyl)-ethyl]phenyl 4-methylbenzoate hydrochloride or 4-[2-dimethylamino-1-(1-hydroxycyclohexyl)-ethyl]phenyl 4-methoxybenzoate succinate or 4-[2-dimethylamino-1-(1-hydroxycyclohexyl)-ethyl]phenyl benzoate hydrochloride | 23% |
| Microcrystalline cellulose | 58% |
| Hydroxypropylmethyl cellulose | 5% |
| Calcium hydrogen phosphate dihydrate | 12% |
| Magnesium stearate | 0.8% |
| Anhydrous colloidal silicon dioxide | 1.2% |

These components were directly tableted to obtain tablets containing drug 100 mg per tablet (calculated based on 1-[2-dimethylamino-1-(4-hydroxyphenyl) -ethyl]cyclohexanol). The results of dissolution test of this kind of tablets are shown as follows.

TABLE 3

Dissolution of normal oral tablets

| | | Dissolution time (h) | | |
|---|---|---|---|---|
| | | 2 | 4 | 8 |
| Dissolution percentage (%) | 4-methylbenzoate | 43.1 | 68.2 | 88.5 |
| | 4-methoxybenzoate | 53.6 | 78.2 | 92.8 |
| | Benzoate | 45.8 | 76.3 | 93.6 |

EXAMPLE 9

Preparation of Sustained Release Capsules of 4-[2-Dimethylamino-1-(1-Hydroxycyclohexyl)-Ethyl] Phenyl 4-Methylbenzoate Hydrochloride for Oral Administration A. Granulation:

| | |
|---|---|
| 4-[2-dimethylamino-1-(1-hydroxycyclohexyl)-ethyl]phenyl 4-methylbenzoate hydrochloride | 40% |
| Microcrystalline cellulose | 59% |
| Hydroxypropylmethyl cellulose | 1% |

The granulation was performed by normal fluidized bed.

B. Coating:

| | |
|---|---|
| Ethyl cellulose | 85% |
| Hydroxypropylmethyl cellulose | 15% |

After the coating was dried, the coated granules were loaded in hard gelatin capsules, and there is 100 mg drug in per capsule (calculated based on 1-[2-dimethylamino-1-(4-hydroxyphenyl)-ethyl]cyclohexanol), and the coating degree was 6%. The dissolution test of the capsules was conducted according to the method of the Pharmacopoeia of People's Republic of China, and the results are as follows.

TABLE 4

Dissolution test of sustained release capsules of 4-[2-dimethylamino-1-(1-hydroxycyclohexyl)-ethyl]phenyl 4-methylbenzoate hydrochloride for oral administration

| | Dissolution time (h) | | | | |
|---|---|---|---|---|---|
| | 2 | 4 | 8 | 12 | 24 |
| Dissolved drug (%) | 5.7 | 27.8 | 61.1 | 79.9 | 96.2 |

EXAMPLE 10

Preparation of Sustained Release Capsules of 4-[2-Dimethylamino-1-(1-Hydroxycyclohexyl)-Ethyl] Phenyl Benzoate Hydrochloride for Oral Administration The preparation method was identical to that of Example 9, except that 4-[2-dimethylamino-1-(1-hydroxycyclohexyl)-ethyl]phenyl 4-methylbenzoate hydrochloride was replaced with 4-[2-dimethylamino-1-(1-hydroxycyclohexyl)-ethyl]phenyl benzoate hydrochloride. The dissolution test of the capsules was conducted according to the method of the Pharmacopoeia of People's Republic of China, and the results are as follows.

TABLE 5

Dissolution test of sustained release capsules of 4-[2-dimethylamino-1-(1-hydroxycyclohexyl)-ethyl]phenyl benzoate hydrochloride for oral administration

| | Dissolution time (h) | | | | |
|---|---|---|---|---|---|
| | 2 | 4 | 8 | 12 | 24 |
| Dissolved drug (%) | 3.8 | 19.8 | 41.2 | 63.8 | 88.2 |

EXAMPLE 11

Preparation of Sustained Release Capsules of 4-[2-Dimethylamino-1-(1-Hydroxycyclohexyl)-Ethyl] Phenyl 4-Methoxybenzoate Succinate for Oral Administration The preparation method was identical to that of Example 9, except that 4-[2-dimethylamino-1-(1-hydroxycyclohexyl)-ethyl]phenyl 4-methylbenzoate hydrochloride was replaced with 4-[2-dimethylamino-1-(1-hydroxycyclohexyl)-ethyl]phenyl 4-methoxybenzoate succinate. The dissolution test of the capsules was conducted according to the method of the Pharmacopoeia of People's Republic of China, and the results are as follows.

TABLE 5

Dissolution test of the sustained release capsules of 4-[2-dimethylamino-1-(1-hydroxycyclohexyl)-ethyl]phenyl 4-methoxybenzoate succinate for oral administration

| | Dissolution time (h) | | | | |
|---|---|---|---|---|---|
| | 2 | 4 | 8 | 12 | 24 |
| Dissolved drug (%) | 6.8 | 24.2 | 56.7 | 83.2 | 97.3 |

EXAMPLE 12

Preparation of Sustained Release Tablets for Oral Administration

A. Tabletting:

| | |
|---|---|
| 4-[2-dimethylamino-1-(1-hydroxycyclohexyl)-ethyl]phenyl 4-methylbenzoate hydrochloride or 4-[2-dimethylamino-1-(1-hydroxycyclohexyl)-ethyl]phenyl 4-methoxybenzoate succinate or 4-[2-dimethylamino-1-(1-hydroxycyclohexyl)-ethyl]phenyl benzoate hydrochloride | 28% |
| Microcrystalline cellulose | 60% |
| Hydroxypropylmethyl cellulose | 10% |
| anhydrous Colloidal silicon dioxide | 0.8% |
| Magnesium stearate | 1.2% |

B. Coating:

| | |
|---|---|
| Ethyl cellulose | 72% |
| Hydroxypropylmethyl cellulose | 12% |
| Dibutyl sebacate | 15% |
| Polyethylene glycol 400 (Macrogol) | 1% |

Each tablet contained 100 mg principal agent (calculated based on 1-[2-dimethylamino-1-(4-hydroxyphenyl)-ethyl]- cyclohexanol). The dissolution test of the tablets was conducted according to the method of the Pharmacopoeia of People's Republic of China, and the results are as follows.

TABLE 6

Dissolution test of the sustained release tablets for oral administration

|  |  | Dissolution time (h) | | | | |
| --- | --- | --- | --- | --- | --- | --- |
|  |  | 2 | 4 | 8 | 12 | 24 |
| Dissolved drug (%) | 4-Methylbenzoate | 12.2 | 33.8 | 58.1 | 79.8 | 98.6 |
|  | 4-Methoxybenzoate | 16.6 | 45.2 | 69.3 | 89.1 | 97.2 |
|  | Benzoate | 6.6 | 21.6 | 50.6 | 68.5 | 87.6 |

EXAMPLE 13

Beagle Test of Sustained Release Capsules of 4-[2-Dimethylamino-1-(1-Hydroxycyclohexyl)-Ethyl]-Phenyl 4-Methylbenzoate Hydrochloride for Oral Administration Six beagles with body weight between 9.8 kg and 12.5 kg were used in this test. They were subjected to overnight fasting, except for water, but ate at 60 minutes before the test, wherein three beagles separately were orally administered with one sustained release capsule of 4-[2-dimethylamino-1-(1-hydroxycyclohexyl)-ethyl]-phenyl 4-methylbenzoate hydrochloride which contained 159 mg drug (100 mg as calculated based on 1-[2-dimethylamino-1-(4-hydroxyphenyl)-ethyl]-cyclohexanol), while the other three beagles separately were intravenously administered with 4-[2-dimethylamino-1-(1-hydroxycyclohexyl)-ethyl]-phenyl 4-methylbenzoate hydrochloride which contains 79 mg drug (50 mg as calculated based on 1-[2-dimethylamino-1-(4-hydroxyphenyl)-ethyl]-cyclohexanol). The blood samples were collected separately at 0.25, 0.5, 1, 2, 4, 6, 8, 12, 16 and 24 hours after drug administration. The blood sample (3 mL) was placed in a test tube with 5 mL heparin, centrifuged at lower temperature and preserved at −70° C., and then analyzed by HPLC-MS (Ther. Drug Monit. 16:100-107 (1994)).

The analysis results of blood samples indicate the orally administrated 4-[2-dimethylamino-1-(1-hydroxycyclohexyl)-ethyl]-phenyl 4-methylbenzoate hydrochloride was quickly converted into 1-[2-dimethylamino-1-(4-hydroxyphenyl)-ethyl]cyclohexanol in vivo.

The data of 1-[2-dimethylamino-1-(4-hydroxyphenyl)-ethyl]-cyclohexanol (compound III) in beagle bodies are shown in Table 7.

TABLE 7

BEAGLE TEST OF 4-[2-DIMETHYLAMINO-1-(1-HYDROXYCYCLOHEXYL)-ETHYL]-PHENYL 4-METHYLBENZOATE HYDROCHLORIDE

|  | AUC (ng * hr/mL) | $C_{max}$ (ng/mL) | $t_{max}$ (hr) | Absolute bioavailability (%) |
| --- | --- | --- | --- | --- |
| Capsule (100 mg) | 2793 | 278 | 5.4 | 89.3 |
| Intravenous injection (50 mg) | 1564 | — | — | — |

EXAMPLE 14

Beagle Test of Orally Administered Sustained Release Capsules of 4-[2-Dimethylamino-1-(1-Hydroxycyclohexyl)-Ethyl]-Phenyl Benzoate Hydrochloride The test was conducted according to the same method of Example 13, wherein each sustained release capsule contained 154 mg drug (100 mg as calculated based on 1-[2-dimethylamino-1-(4-hydroxyphenyl)-ethyl]-cyclohexanol). The analysis results of blood samples also indicate the orally administrated 4-[2-dimethylamino-1-(1-hydroxycyclohexyl)-ethyl]-phenyl benzoate hydrochloride was quickly converted into 1-[2-dimethylamino-1-(4-hydroxyphenyl)-ethyl]-cyclohexanol in vivo.

The data of 1-[2-dimethylamino-1-(4-hydroxyphenyl)-ethyl]-cyclohexanol (compound III) in beagle bodies are shown in Table 8.

TABLE 8

Beagle test of 4-[2-dimethylamino-1-(1-hydroxycyclohexyl)-ethyl]-phenyl benzoate hydrochloride

| AUC (ng * hr/mL) | $C_{max}$ (ng/mL) | $t_{max}$ (hr) | Absolute bioavailability (%) |
| --- | --- | --- | --- |
| 2536 | 267 | 5.7 | 81.1 |

EXAMPLE 15

Beagle Test of Orally Administered Sustained Release Capsules of 4-[2-Dimethylamino-1-(1-Hydroxycyclohexyl)-Ethyl]-Phenyl 4-Methoxybenzoate Succinate The test was conducted according to the same method of Example 13, wherein each sustained release capsule contained 195 mg drug (100 mg as calculated based on 1-[2-dimethylamino-1-(4-hydroxyphenyl)-ethyl]-cyclohexanol).

The analysis results of blood samples also indicate the orally administrated 4-[2-dimethylamino-1-(1-hydroxycyclohexyl)-ethyl]-phenyl 4-methoxybenzoate succinate was quickly converted into 1-[2-dimethylamino-1-(4-hydroxyphenyl)-ethyl]-cyclohexanol in vivo.

The data of 1-[2-dimethylamino-1-(4-hydroxyphenyl)-ethyl]-cyclohexanol (compound III) in beagle bodies are shown in Table 9.

TABLE 9

Beagle test of 4-[2-dimethylamino-1-(1-hydroxycyclohexyl)-ethyl]-phenyl 4-methoxybenzoate succinate

| AUC (ng * hr/mL) | $C_{max}$ (ng/mL) | $t_{max}$ (hr) | Absolute bioavailability (%) |
| --- | --- | --- | --- |
| 2668 | 287 | 4.6 | 85.3 |

The various embodiments described above can be combined to provide further embodiments. All of the U.S. patents, U.S. patent application publications, U.S. Patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A compound of formula (I), an optical isomer or a pharmaceutically acceptable salts thereof,

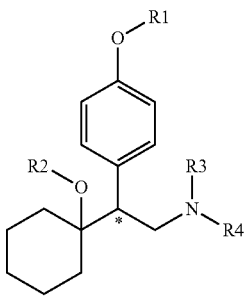

(I)

wherein,
chiral center (*) can be R or S or RS (racemic mixture);
R1 is aryloyl represented by

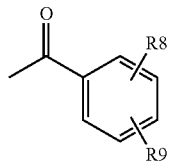

wherein R8 and R9 are independently selected from hydrogen, saturated alkyl having 1-6 carbon atoms, or alkoxyl having 1-6 carbon atoms, unsaturated alkyl having 2-6 carbon atoms, OH, Cl, F, CN, carboxyl and ester group having 1-6 carbon atoms;

R2 is hydrogen, or aryloyl having 7-20 carbon atoms; and

R3 and R4 are independently hydrogen, saturated alkyl having 1-20 carbon atoms, unsaturated alkyl having 2-20 carbon atoms, aryl having 6-20 carbon atoms with substituent having 1-10 carbon atoms, substituted or unsubstituted phenyl or benzyl; cycloalkyl having 4-10 carbon atoms, hydroxyalkyl, carbohydrate having 1-10 carbon atoms, or C1-C10 alkyl containing one or more heteroatoms selected from oxygen, nitrogen, fluorine, sulfur, and phosphor.

2. The compound of formula (I) according to claim 1, characterized in that the substituents R8 and R9 are independently selected from hydrogen, methyl, ethyl, methoxy, ethoxy, fluorine or carboxyl.

3. The salt of the compound of formula (I) according to claim 1, characterized in that the salt of the compound is hydrochloride, sulfate, maleate, succinate, and a salt formed with other pharmaceutically acceptable acid.

4. A pharmaceutical composition comprising a compound, its optical isomer or pharmaceutically acceptable salt according to claim 1, and a pharmaceutically acceptable carrier.

5. The pharmaceutical composition according to claim 4, the said composition is used in a manner of oral, injection, transdermal, nasal, mucous or inhalation administration.

6. The pharmaceutical composition according to claim 4, the said composition is a normal, sustained release, controlled release, site-specific or fast release dosage form.

* * * * *